United States Patent [19]
Goof

[11] Patent Number: 5,252,303
[45] Date of Patent: Oct. 12, 1993

[54] APPARATUS FOR STERILIZING OBJECTS HAVING CHAMBER WALL AS HEATER

[76] Inventor: Sven K. L. Goof, 236A, Gl. Strandvej, DK-3050 Humlebaek, Denmark

[21] Appl. No.: 896,742

[22] Filed: Jun. 9, 1992

Related U.S. Application Data

[63] Continuation of Ser. No. 360,053, filed as PCT/DK88/00160 on Oct. 3, 1988, abandoned.

[30] Foreign Application Priority Data

Oct. 2, 1987 [DK] Denmark .............................. 5174/07

[51] Int. Cl.⁵ .......................... A61L 2/06; A61L 2/24
[52] U.S. Cl. ..................... 422/292; 219/438; 219/457; 219/521; 219/536; 422/22; 422/26; 422/295; 422/299; 422/109
[58] Field of Search .................. 422/22, 26, 292, 295, 422/307, 109, 299; 219/221, 275, 311, 336, 438, 451, 457, 459, 521, 536

[56] References Cited

U.S. PATENT DOCUMENTS

| | | | |
|---|---|---|---|
| 3,436,171 | 4/1969 | Weichselbaum et al. | 422/307 |
| 3,861,872 | 1/1975 | MacFarlane | 21/56 |
| 4,331,859 | 5/1982 | Thomas et al. | 219/521 |
| 4,419,568 | 12/1983 | Van Overloop | 219/441 |
| 4,481,410 | 11/1984 | Bortnick | 219/521 |
| 4,578,566 | 3/1986 | Bowen | 219/521 |
| 4,582,076 | 4/1986 | Prat | 134/57 R |
| 4,659,911 | 4/1987 | Ryder et al. | 219/521 |

FOREIGN PATENT DOCUMENTS

| | | |
|---|---|---|
| 0083807 | 12/1984 | European Pat. Off. . |
| 3236635 | 4/1984 | Fed. Rep. of Germany . |
| 3516495 | 11/1986 | Fed. Rep. of Germany . |
| 18083 | of 1898 | United Kingdom . |

Primary Examiner—James C. Housel
Assistant Examiner—Arlen Soderquist
Attorney, Agent, or Firm—Tilton Fallon Lungmus

[57] ABSTRACT

An apparatus for sterilizing objects comprising a tubular container part which is removably arranged on an electric supply and control unit. The container part has a chamber-defining inner wall which is also an electrical resistance heating element. Accordingly, the container part may be made with low heat capacity and a correspondingly short heat-up period.

4 Claims, 2 Drawing Sheets

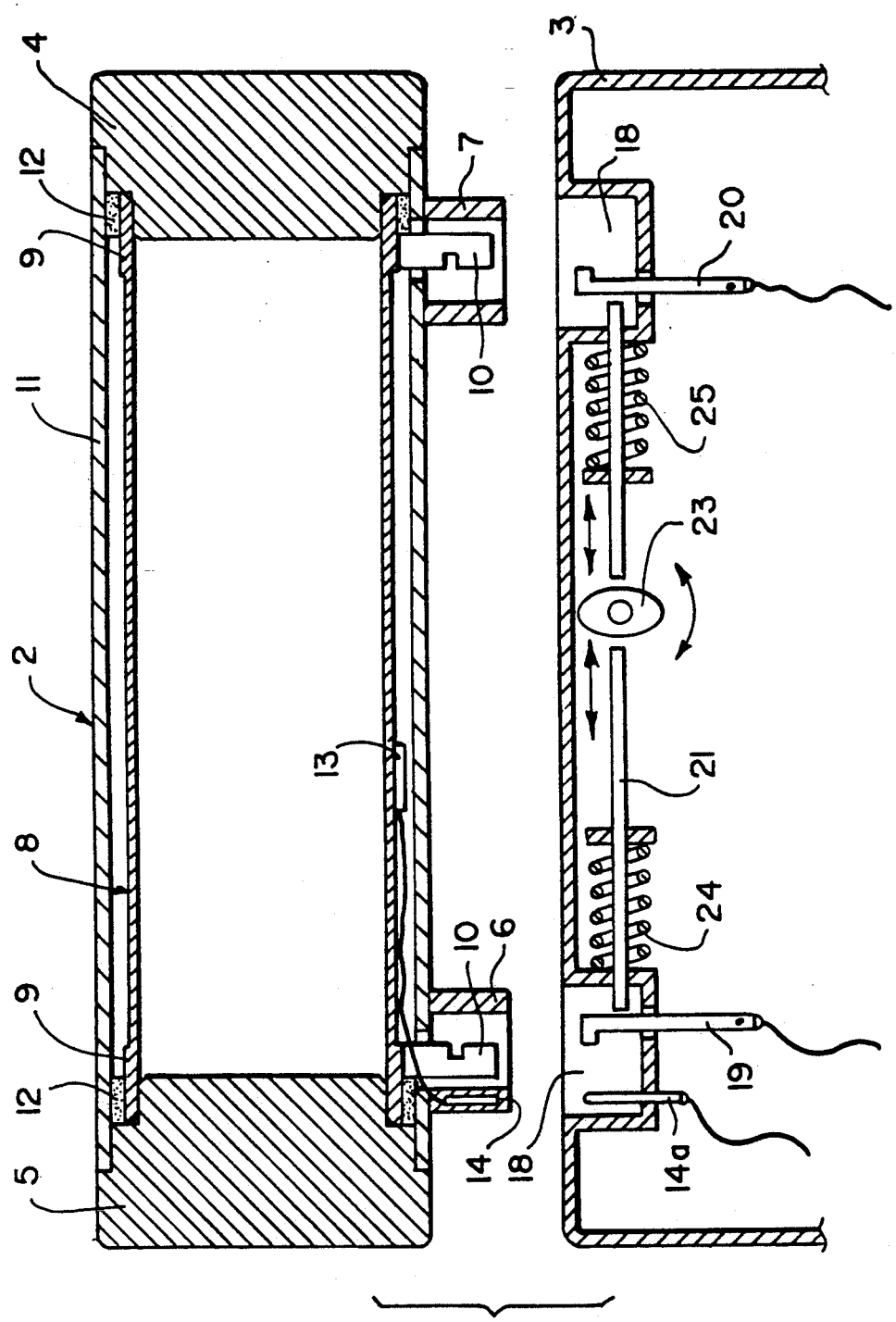

APPARATUS FOR STERILIZING OBJECTS HAVING CHAMBER WALL AS HEATER

This application is a continuation of application Ser. No. 360,053, filed Jun. 1, 1989, now abandoned, which is a continuation of PCT International Application No. PCT/DK88/00160, having an International filing date of Oct. 3, 1988, now abandoned.

The present invention relates to an apparatus for sterilizing objects, in Particular dental and medical utensil.

In connection with various types of clinical patient treatments, it is presently a general trend that society is making ever increasing demands as regards hygiene and infection safety. Especially in connection with dental treatments the patients as well as the clinical staff are making greatly increasing demands for efficient and optimum infection protection.

Many medical and dental utensils are frequently in direct contact with blood and saliva, and sterilization before each patient treatment is necessary to ensure the hygienic conditions and patient safety.

The most widespread method is steam sterilization which is performed in autoclaves and takes place in saturated steam under pressure.

Typical autoclaving conditions are temperatures in the range of 120-140 degrees Celsius with associated steam pressures in the area of 1-3 bars overpressure. At such conditions the sterilization phase itself requires a period of time from about 20 min. (at 120 degrees Celsius) and down to about 5 min. (at 140 degrees Celsius). In addition there are substantial time consumptions for a preceding heat-up and sterilization period and for a subsequent cool-down period.

The durations of the heat-up and cool-down periods are determined by the construction of the autoclave equipment. Conventional autoclaves for every day use in clinics are bulky and heavy structures with quite thick chamber walls in which electrical resistance heating wires are embedded.

The great heat capacity of such chamber walls causes the heat-up and cool-down periods to be very long. In addition the regulation of the chamber temperature during the sterilization period becomes both slow and difficult because of the high thermal inertia of the system.

The long heat-up and cool-down periods represent a very substantial additional time which very often is in the order of 40-50 minutes. The result is that a conventional autoclave only is able to make 7-8 complete steam sterilizations per day, at the most.

Consequently, continuous standard patient treatment in a dental clinic will require at least 6-8 complete kits of instruments in order to be able to operate with optimum instrument hygiene. In addition conventional autoclaves for clinics are relatively expensive as regards both purchase and operation as well.

The demands as to optimum hygiene is accordingly tied up with substantial equipment investments. The reason of that is basicly the long total process time which is due to the heavy walls with high heat capacities and a relatively big chamber volume (typically 10-30 liters) of conventional autoclaves.

The slow and frequently insufficient control and regulation of the chamber temperature is also a substantial drawback of conventional autoclaves. On one hand it is a principal condition that the temperature anywhere in the chamber must r the desired sterilization temperature (for example 120 degrees Celsius) throughout the complete sterilization period (for example 20 min.). On the other hand it is very important that the temperature at no time and at no place in the chamber rises substantially above the desired preset value. The result of even shorter temperature increases to over-temperatures may be thermal damages to temperature sensitive elements, such as objects or instrument parts made of plastic.

Again, the reasons are the heavy chamber walls which are difficult to give and to maintain at a constant uniform surface temperature anywhere in the chamber. Moreover, the chamber volume usually used has a shape and size which make it difficult to provide and maintain a uniform temperature distribution in the interior of the chamber by means of heating elements which are embedded in the chamber walls.

With a view to reducing the cool-down period it is known to provide conventional autoclaves with a pressure relief valve, whereby the hot saturated steam is relieved from the chamber immediately after the termination of the sterilization period.

In itself this will result in a substantial reduction of the cool-down period, but on the other hand it has appeared that such a rapid pressure relief may be connected with a special drawback.

Thus, it has been found that, immediately after the relief, a temporary, uncontrolled rise may occur in the chamber temperature relative to the preset temperature value which had been stabilized during the sterilization period. Most often, such a temporary rise in chamber temperature which can be in the order of 10-20 degrees Celsius, will appear unnoticed. Assumably this temperature rising—and the resulting excess temperatures has been the reason of, otherwise incomprehensible, thermal damages to plastic objects which were believed to have been sterilized at the correct temperature, but nevertheless showed marked damages.

Again, the reason of the phenomena is probably to be found in the heavy chamber walls with large contents of heat and varying temperature distribution. Moreover a contributory reason may be the fact that a relatively large volume of superheated saturated steam is suddenly removed from a large and inert system in thermal balance.

Summarizing, there is consequently a great demand of a sterilizer or autoclave of the type under consideration which is not encumbered with the drawbacks mentioned above, and by means of which objects can be sterilized, in particular steam sterilized as efficiently as, but substantially quicker than, in conventional autoclaves.

In particular there is a great demand of a sterilizer having a chamber shape and chamber heating means which are designed with a special view to providing a rapid and reliable establishment of a uniform chamber wall temperature as well as a homogeneous roan temperature distribution in the interior of the sterilizer chamber.

It is the principal object of this invention to meet the above mentioned demands and to that end, the invention provides a an improved sterilizer.

In the apparatus of the invention the chamber defining walls can be utilized as a heating element. In the container chamber there is obtained a wall surface temperature which is substantially more uniform compared to conventional constructions, wherein a number of wire shaped or rod shaped heating elements are embedded more or less uniformly distributed in the chamber walls.

In addition the uniform surface temperature is provided directly as a consequence of the design of the heating element, and hence without any need of supplementing and surrounding the heating element with thick temperature—smoothing walls, such as is the case in conventional autoclaves.

In the apparatus of the invention the complete container structure can in other words be made as a thin-walled structure with low heat capacity. As a result of this, the apparatus of the invention can be heated to and stabilized at a desired sterilization temperature within a very few minutes. Moreover, the sterilization temperature can be maintained with a very short response time in the temperature controlling and, consequently, with a higher accuracy.

In accordance with the invention it is preferred that the electrically conducting wall is tubular and is provided with electrical connectors or terminals at opposite ends thereof. Thereby is obtained the best possible conditions of a homogeneous temperature distribution in the interior of the tube and, thereby, in the sterilizer chamber.

In the preferred embodiment of the invention, the electrically conducting wall is defining an inner wall of the container part. This means that the chamber—defining walls can be defined directly by the conducting wall which operates as heating element.

In the following the present invention will be described in further details with references to the drawings in which:

FIG. 2 is a partial longitudinal sectional view which schematically illustrates a removable container part as well as a section of a power supply part of the embodiment of FIG. 1.

Figure 1:
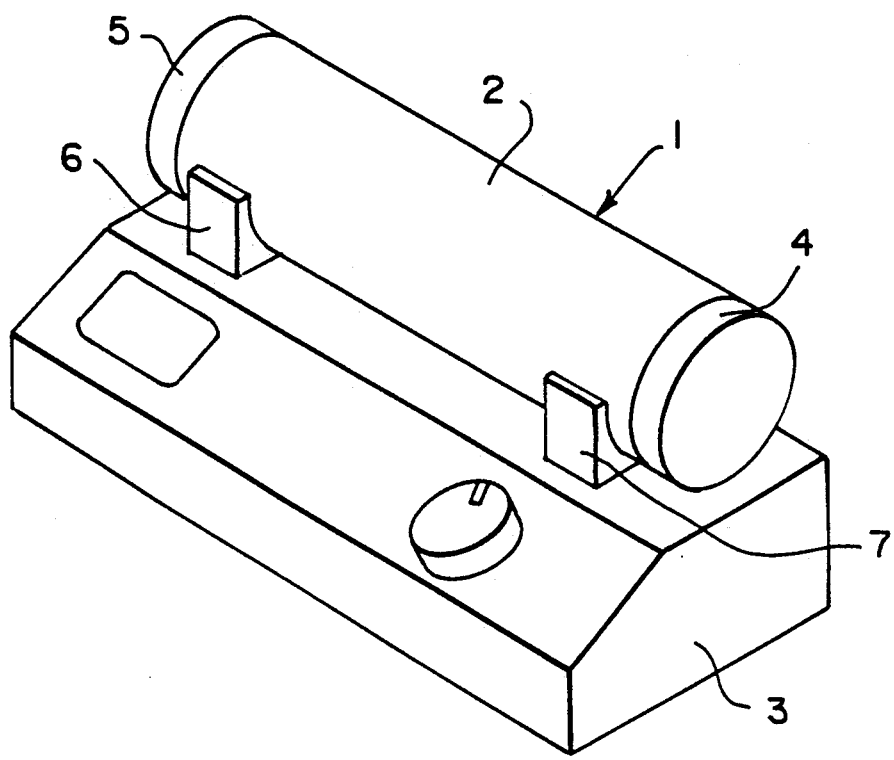
FIG. 1 shows an embodiment of the sterilizer apparatus of the invention.

In the drawings FIG. 1 is showing a sterilizer apparatus 1 according to this invention. The main constituent parts are a container part 2 and a power supply and controller unit 3. The container part as shown is tubular with closed ends of which at least one end is arranged as a removable end cover 4. As shown the other end may be closed by means of a similar end cover 5 which, however, does not have to be removable. With end cover 4 correctly seated the container part 2 will be closed in a pressure-proof manner.

The container part 2 is arranged with two supports 6,7 which also include means for providing respective electric connections with the supply unit 3. Preferably the supports 6,7 are permanently attached to the container part. On the other hand the connections with the supply unit 3 are preferably detachable, so that the container part 2 can be released and be lifted free of the unit 3.

Referring now to FIG. 2 the container part 2 comprises a special inner tube 8 which, together with the end covers 4,5 defines a sterilization chamber. In accordance with the main aspect of this invention the inner tube 8 is also utilized as electric resistance heating element. For that purpose the inner tube 8 is provided with respective electrical connections at the opposite tube ends.

In the embodiment shown each of these connections comprises an annular tube part 9 and a contact member 10 connected therewith. The contact member 10 extends into the interior of a slot or cavity in the corresponding support 6,7, respectively.

Each of the annular tube parts 9 has a bigger wall thickness than the inner tube 8 so that an electric current supplied through the contact member 10, will be effectively and uniformly distributed circumferentially of the inner tube 8. The result is a uniform current density through the entire cross section of the inner tube.

The inner tube 8 is made of an electrically conducting material, preferabley of stainless steel. In order to provide an electrical resistance through the inner tube 8 which is sufficient to provide the needed heating power, the inner tube 8 has a relatively small wall thickness, for example 0.2 mm. In the example shown in FIG. 2 the appropriate wall thickness has been provided by turning down the tube 8, wherby the respective tube end parts 9 can be made at the same time. Alternatively each of the end parts 9 can be a separately made ring which has been permanently attached to the respective ends of the thinner tube 8.

In the embodiment shown the inner tube 8 is inserted coaxially in a surrounding outer tube 11, and electrically insulating spacer members 12 keeping the two tubes separated. In principle, such an outer tube or a corresponding outer casing is not necessary, but is preferred for practical reasons.

The outer tube 11 may be made of metal or of plastic materials, and the spacing between the inner and outer tubes may be filled with an appropriate heat insulating material. In the spacing there may, moreover, be arranged one or more temperature sensors 13 which communicate with respective associated plug sockets 14 in the supports 6,7 through respective wires.

The supports 6,7 and the end covers 4,5 are preferably made of an appropriate temperature resistant plastic material. As already indicated, one of the end covers may be permanently attached, and it may, moreover, be provided with means (not shown) for measuring or indicating the pressure in the interior of the container part 2. Furthermore, this end cover may be provided with valve means for manual and/or automatical relief of the pressure in the container part.

The other, removable end cover 4 must close in a pressure-proof manner, and it has not shown locking means which are releasable, for example by turning the end cover.

Figure 3:
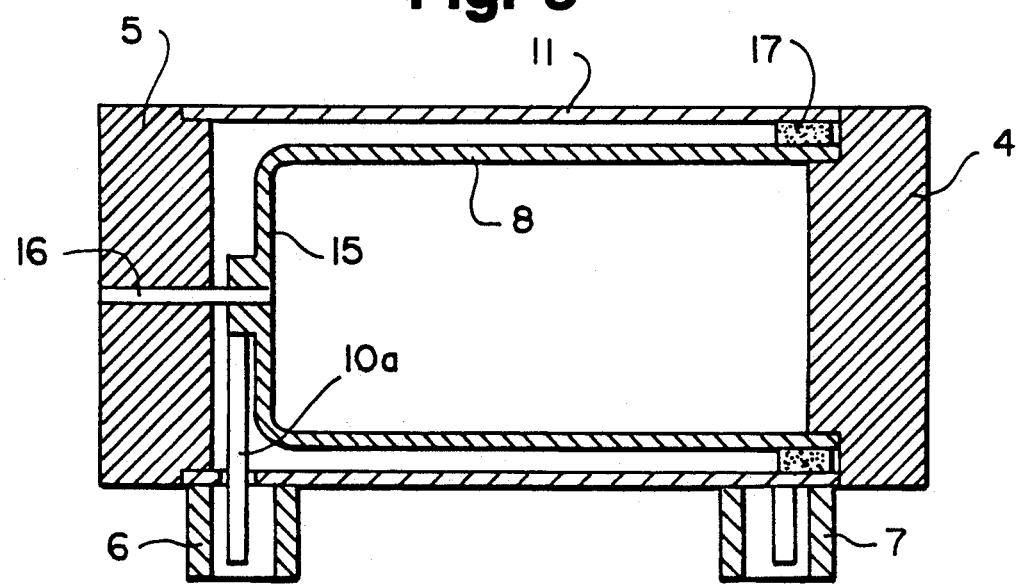
FIG. 3 is a longitudinal sectional view schematically showing an alternative embodiment of the container part.

FIG. 3 shows schematically an alternative embodiment of the removable container part 2. The inner tube 8 is still a thin-walled tube which also operates as electric resistance heating element. One end of the inner tube is however provided with a permanent end plate 15 which centrally carries an axially projecting pin or stud 16.

The stud 16 is in connection with a contact member 10a in FIG. 2 and extending into the support 6. The stud 16 may be shaped as a pipe spigot communicating with the chamber in the inner tube 8. Thereby the stud or spigot 16 can be part of the above mentioned means for measuring and relieving the pressure in the chamber.

The opposite end of the inner tube 8 is permanently connected with the outer tube 11 by means of a spacer ring 17 which also serves as current distributor ring similar to the tube end part 9 in FIG. 2. for that purpose the spacer ring 17 is in connection with the contact member 10 in the support 7.

Each of the supports 6,7 is arranged as an electric plug or connector for removable connection with a corresponding connector or socket on the power supply and controller unit 3.

Referring to FIG. 2, the schematically shown embodiment of the unit 3 includes respective recesses 18 which can receive the supports 6,7. In each recess is arranged a resilient contact tongue 19,20 respectively which, when the supports have been seated, extends along the associated contact member 10, but separated therefrom. At the same time as the supports 6,7 are being seated, the socket 14, and other similar plugs if any, are engaging respective corresponding plug means 14a.

In the embodiment shown there is, consequently, no electric connection between the contact members 10 and the respective contact tongues 19,20, when the supports 6,7 are seated in the recessed 18. The electric contact is not provided until a special locking mechanism which can be activated manually, has been operated.

Upon activating the locking mechanism the contact tongues 19,20 are pressed or bent to engage the contact members 10. In addition to providing electric connections the contact tongues and contact members may also be designed to provide mechanical retainment of the supports 6,7 and, thereby, of the complete container part 2 relative to the supply unit 3.

The release of the locking mechanism takes place automatically, when an adjustable time period which corresponds to a desired sterilization period, has expired. When the locking mechanism releases, there will, accordingly, also be an interruption of the current for the heating element, that is the inner tube 8 in the container part 2.

In FIG. 2 the schematically shown locking mechanism comprises two push rods 21, 22, each rod having one end in engagement with the periphery of an elliptical disk 23 which can be rotated manually in order to push the rods axially outwardly for engaging the respective contact tongues 19,20. During this fuming or activation of the disk 23, respective return springs 24,25 and a (not shown) torsion spring tends to rotate the disk 23 back to its starting position.

The locking mechanism is retained in activated condition by means of a (not shown) latch which is electrically controlled. When the latch is released, the respective springs will bring the locking mechanism back to its starting position, wherein the container part 2 is free to be removed.

Obviously, the locking mechanism must not provide any possibility of short-circuiting between the contact tongues 19,20. In the embodiment shown the push rods 21,22 can therefor appropriately be made completely or in part of plastic material.

The contact tongues 19,20 are connected with the secondary of a transformer in the supply unit 3 which also includes appropriate control and regulating circuits which are able to communicate with the container part 2 through plug connectors similar to socket 14 and plug 14a.

When using the apparatus of this invention the objects are placed for sterilization in the container part 2, and an appropriate dosage of water is introduced into the sterilization chamber. The water can be introduced by removing the end cover 4 or through a special conduit in that cover. In either case the dosing can appropriately be made by means of a hypodermic syringe.

Therafter the charged and closed container part 2 is placed on the supply unit 3, and the desired sterilization period and temperature is adjusted. Then the locking mechanism is activated by fuming the disk 23, and the process starts.

The introduced quantity of water will evaporate and create a pressure corresponding to the steam pressure at the preset temperature.

When the preset period of time has expired, the container part 2 will be released, and it can be replaced by another container part which can be sterilized while the first container part is placed for cooling.

Accordingly it is beneficial to have several container parts 2 for each supply unit 3. The container parts are also well-suited for storing and transporting the sterilized instruments.

Because of the special container part 2 the heat-up and cool-down periods can be reduced to a few minutes. Moreover, the result is a very uniform and precisely controlled temperature during the sterilization period, whereby excess temperatures are effectively avoided.

All things considered, this invention provides a sterilizer which is very useful and suitable for daily use in clinics compared to conventional autoclaves which, in addition, involve substantially bigger investments in equipment and instruments.

I claim:

1. Apparatus for sterilizing objects comprising a container part including a sterilization chamber having means for opening and closing said chamber for depositing and removing objects therefrom and for introducing a quantity of liquid therein, and means for controlled electrical heating of the interior of said chamber, wherein the improvement comprises said sterilization chamber defined by a tubular electrically-conductive wall extending longitudinally with respect to said chamber and a pair of opposite end walls means at opposite ends of said electrically-conductive wall for connecting an electrical heat-generating current therethrough, and the material of said electrically-conductive wall forming an electrical resistance heating element of said means for electrical heating of the interior of said chamber.

2. The apparatus according to claim 1 in which an outer casing surrounds said electrically-conductive wall.

3. The apparatus according to claims 1 and 2 in which said means for controlled electrical heating comprises a power supply and controller unit, and means for releasably and electrically coupling said power supply and controller unit to said container part.

4. The apparatus according to claim 3 in which said means for releasably and electrically coupling said power supply and controller unit to said container part includes electrically-controlled locking means for automatically releasing said container part and interrupting the electrical connection thereto after the expiration of a selected time interval.

* * * * *